(12) United States Patent
Barton et al.

(10) Patent No.: US 11,396,604 B1
(45) Date of Patent: Jul. 26, 2022

(54) SELF-REPAIRING POLYMERIC COATINGS

(71) Applicants: SWIMC LLC, Cleveland, OH (US); THE UNIVERSITY OF AKRON, Akron, OH (US)

(72) Inventors: Hazel A Barton, Akron, OH (US); Kathleen R. Gisser, Cleveland, OH (US); Tony A. Rook, Cleveland, OH (US)

(73) Assignees: SWIMC LLC, Cleveland, OH (US); The University of Akron, Akron, OH (US)

( * ) Notice: Subject to any disclaimer, the term of this patent is extended or adjusted under 35 U.S.C. 154(b) by 443 days.

(21) Appl. No.: 16/420,286

(22) Filed: May 23, 2019

Related U.S. Application Data (60) Provisional application No. 62/675,344, filed on May 23, 2018.

(51) Int. Cl.
| | |
|---|---|
| *C09D 5/00* | (2006.01) |
| *C09D 163/00* | (2006.01) |
| *C09D 113/02* | (2006.01) |
| *C12P 3/00* | (2006.01) |
| *C09D 175/04* | (2006.01) |

(52) U.S. Cl.
CPC .............. *C09D 5/00* (2013.01); *C09D 113/02* (2013.01); *C09D 163/00* (2013.01); *C09D 175/04* (2013.01); *C12P 3/00* (2013.01)

(58) Field of Classification Search
CPC ...... C09D 5/00; C09D 113/02; C09D 163/00; D09D 175/04; C12P 3/00

USPC ....................................................... 428/411.1
See application file for complete search history.

(56) References Cited

PUBLICATIONS

Mikusova et al., International Journal of Polymeic Materials and Polymeric Biomaterials, 68, 4, 152-159, 2019. (Year: 2019).*
Dhami et al., J. Microbiol. Biotechnol., 23(5), 707-714, 2013. (Year: 2013).*

* cited by examiner

*Primary Examiner* — Hui H Chin
(74) *Attorney, Agent, or Firm* — Renner Kenner Greive Bobak Taylor & Weber (57) ABSTRACT

A coating composition may include a polymeric binder and bacteria that exhibit biologically induced mineralization (BIM) or biologically controlled mineralization (BCM) of calcium carbonate ($CaCO_3$) in the presence of environmental calcium. The bacteria may exhibit BIM or BCM of $CaCO_3$ using the ChaA antiporter protein. The coating formulations may be used to form coatings that exhibit self-healing properties in response to damage, such as a cut, tear, puncture, abrasion, or the like. For example, in response to being exposed to the damage, the bacteria may utilize nutrients, a calcium source, and water to cause precipitation of $CaCO_3$ at the site of the damage. The nutrients, the calcium source, and the water may be provided as part of the coating formulation, as part of another layer of a coating system, from an external source (e.g., an applied spray or wash), or combinations thereof.

19 Claims, 4 Drawing Sheets

Self-healing paint proof-of-concept. A) crack introduced into a 20 μm thick-paint film (microbes can be seen growing along the edge of the film – black arrows); B) after one week of growth, the calcite precipitation is building up, and even occluding (white arrows) the crack; C) transmitted light, close up image shows the opaque calcite crystals precipitating along the edge of the crack. All scale bars are in μm.

SELF-REPAIRING POLYMERIC COATINGS

STATEMENT REGARDING FEDERALLY SPONSORED RESEARCH OR DEVELOPMENT

This invention was made with Government support under Agreement No. HR0011-18-9-0007, awarded by DARPA. The government has certain rights in the invention.

BACKGROUND

Biologically induced mineralization (BIM) has been used in industrial processes, such as oil production, concrete repair, and preservation of monuments. BIM may result from bacterial species altering the local pH of the environment, increasing the saturation index (SI) and precipitating $CaCO_3$. For example, autotrophic $CO_2$ fixation favors the formation of $CO_3^{2-}$ from $HCO_3^-$, promoting $CaCO_3$ precipitation in the presence of $Ca^{2+}$, while urease-dependent cleavage of urea to $HN_4^+$ raises the local pH to alter the SI of $CaCO_3$ in favor of precipitation. However, BIM may be expensive to mimic and inherently difficult to control.

SUMMARY

In some examples, the disclosure describes a coating composition that includes a polymeric binder and bacteria that exhibit biologically induced mineralization or biologically controlled mineralization of calcium carbonate in the presence of environmental calcium.

In some examples, the disclosure describes an article that includes a substrate and a coating system on the substrate. The coating system includes a coating layer comprising a polymeric binder and bacteria that exhibit biologically induced mineralization or biologically controlled mineralization of calcium carbonate in the presence of environmental calcium.

In some examples, the disclosure describes a method for repairing a coating layer that includes a polymeric binder. The method includes exposing bacteria that exhibit biologically induced mineralization or biologically controlled mineralization of calcium carbonate in the presence of environmental calcium to a calcium source, water, and nutrients at a damaged portion of the coating. The coating layer includes the bacteria, and exposure of the damaged portion of coating layer to the calcium source, water, and nutrients causes the bacteria to excrete calcium ions and bicarbonate ions, inducing precipitation of calcium carbonate at the damaged portion of the coating layer.

In some examples, the disclosure describes a method for forming a self-repairing coating formulation. The method includes mixing bacteria that exhibit biologically induced mineralization or biologically controlled mineralization of calcium carbonate in the presence of environmental calcium in a coating formulation comprising a polymeric binder.

An embodiment of the invention provides a coating composition comprising: a polymeric binder; and bacteria that exhibit biologically induced mineralization or biologically controlled mineralization of calcium carbonate in the presence of environmental calcium.

Another embodiment of the invention provides a coating composition as any embodiment above comprising between about $10^2$ colony forming units per milliliter and about $10^6$ colony forming units per milliliter.

Another embodiment of the invention provides a coating composition as any embodiment above further comprising an aqueous carrier liquid.

Another embodiment of the invention provides an article comprising: a substrate; and a coating system on the substrate, wherein the coating system comprises: a coating layer comprising a polymeric binder and bacteria that exhibit biologically induced mineralization or biologically controlled mineralization of calcium carbonate in the presence of environmental calcium.

Another embodiment of the invention provides a coating composition as any embodiment above wherein the coating layer comprises between about $10^2$ colony forming units per milliliter and about $10^6$ colony forming units per milliliter.

Another embodiment of the invention provides a coating composition as any embodiment above further comprising a calcium source.

Another embodiment of the invention provides a coating composition as any embodiment above wherein the coating layer comprises the calcium source.

Another embodiment of the invention provides a coating composition as any embodiment above further comprising an underlayer or primer coat, wherein the underlayer or primer coat is between the substrate and the coating layer, and wherein the underlayer or primer coat comprises the calcium source.

Another embodiment of the invention provides a coating composition as any embodiment above further comprising nutrients.

Another embodiment of the invention provides a coating composition as any embodiment above wherein the coating layer comprises the nutrients.

Another embodiment of the invention provides a coating composition as any embodiment above comprising between about 0.2 wt. % and about 5 wt. % of the calcium source.

Another embodiment of the invention provides a coating composition as any embodiment above further comprising an underlayer or primer coat, wherein the underlayer or primer coat is between the substrate and the coating layer, and wherein the underlayer or primer coat comprises the calcium source.

Another embodiment of the invention provides a coating composition as any embodiment above further comprising an underlayer or primer coat, wherein the underlayer or primer coat is between the substrate and the coating layer, and wherein the underlayer or primer coat comprises the nutrients.

Another embodiment of the invention provides a method for repairing a coating layer comprising a polymeric binder, the method comprising: exposing bacteria that exhibit biologically induced mineralization or biologically controlled mineralization of calcium carbonate in the presence of environmental calcium to a calcium source, water, and nutrients at a damaged portion of the coating, wherein the coating layer comprises the bacteria, and wherein exposure of the damaged portion of coating layer to the calcium source, water, and nutrients causes the bacteria to excrete calcium ions and bicarbonate ions, inducing precipitation of calcium carbonate at the damaged portion of the coating layer.

Another embodiment of the invention provides a coating composition as any embodiment above wherein exposing the bacteria to the calcium source, water and nutrients comprises applying a solution comprising at least one of the calcium source, water, or the nutrients to a surface of the damaged portion of the coating layer.

Another embodiment of the invention provides a coating composition as any embodiment above wherein applying the solution comprises at least one of spraying the solution or wiping the solution on the surface of the damaged portion of the coating layer.

Another embodiment of the invention provides a coating composition as any embodiment above wherein the solution comprises water and the nutrients, and wherein the coating layer comprises the calcium source.

Another embodiment of the invention provides a coating composition as any embodiment above wherein the solution comprises water and the calcium source, and wherein an underlayer or primer layer comprises the nutrients.

Another embodiment of the invention provides a coating composition as any embodiment above wherein an underlayer or primer layer comprises the nutrients, wherein the coating layer comprises the calcium source, and wherein the solution comprises water.

Another embodiment of the invention provides a coating composition as any embodiment above wherein an underlayer or primer layer comprises the nutrients, wherein the coating layer comprises the calcium source, and wherein an event that forms the damaged portion of the coating layer causes the exposure of the bacteria to the calcium source, water, and nutrients.

Another embodiment of the invention provides a coating composition as any embodiment above wherein the water is present in the underlayer or primer layer or is environmental humidity.

Another embodiment of the invention provides a coating composition as any embodiment above wherein the coating layer comprises the calcium source and the nutrients, and wherein an event that forms the damaged portion of the coating layer causes the exposure of the bacteria to the calcium source, water, and nutrients.

Another embodiment of the invention provides a coating composition as any embodiment above wherein the event that forms the damaged portion exposes bacteria at a surface of the damaged portion to water.

Another embodiment of the invention provides a coating composition as any embodiment above wherein the bacteria are encapsulated in an encapsulant, and wherein an event that forms the damaged portion of the coating layer breaks the encapsulant of bacteria at a surface of the damaged portion of the coating layer.

Another embodiment of the invention provides a coating composition as any embodiment above wherein the coating layer comprises between about $10^2$ colony forming units per milliliter and about $10^6$ colony forming units per milliliter.

Another embodiment of the invention provides a method for forming a self-repairing coating formulation, the method comprising: mixing bacteria that exhibit biologically induced mineralization or biologically controlled mineralization of calcium carbonate in the presence of environmental calcium in a coating formulation comprising a polymeric binder.

Another embodiment of the invention provides a coating composition as any embodiment above further comprising encapsulating the bacteria in an encapsulant prior to mixing the bacteria in the coating formulation.

Another embodiment of the invention provides a coating composition as any embodiment above further comprising mixing a calcium source in the coating formulation.

Another embodiment of the invention provides a coating composition as any embodiment above further comprising mixing nutrients in the coating formulation.

Another embodiment of the invention provides a coating composition as any embodiment above wherein the bacteria comprise vegetative bacteria.

Another embodiment of the invention provides a coating composition as any embodiment above wherein the bacteria comprise spores.

Another embodiment of the invention provides a coating composition as any embodiment above wherein the bacteria comprise Gram-negative bacteria.

Another embodiment of the invention provides a coating composition as any embodiment above wherein the bacteria comprise Gram-positive bacteria.

Another embodiment of the invention provides a coating composition as any embodiment above wherein the bacteria comprise genetically modified bacteria configured to exhibit enhanced calcium transport and secretion.

Another embodiment of the invention provides a coating composition as any embodiment above wherein the bacteria are encapsulated in an encapsulant.

Another embodiment of the invention provides a coating composition as any embodiment above wherein the encapsulant comprises alginate or polydopamine.

Another embodiment of the invention provides a coating composition as any embodiment above wherein the calcium source comprises calcium carbonate particles.

Another embodiment of the invention provides a coating composition as any embodiment above wherein the calcium source comprises an organic calcium salt.

Another embodiment of the invention provides a coating composition as any embodiment above wherein the calcium source comprises an inorganic calcium salt.

Another embodiment of the invention provides a coating composition as any embodiment above wherein the nutrients comprise at least one of a disaccharide, an amino acid, or a carboxylic acid.

Another embodiment of the invention provides a coating composition as any embodiment above wherein the polymeric binder comprises at least one of a (meth)acrylic latex, a vinyl acrylic latex, or a styrene acrylic latex.

Another embodiment of the invention provides a coating composition as any embodiment above wherein the polymeric binder comprises an epoxy.

Another embodiment of the invention provides a coating composition as any embodiment above wherein the polymeric binder comprises a polyurethane.

Another embodiment of the invention provides a coating composition as any embodiment above further comprising an additive.

Another embodiment of the invention provides a coating composition as any embodiment above wherein the additive comprises at least one of a pigment, a colorant, a dispersant, a fungicide, an UV stabilizer, a thickener, a wetting agent, a defoamer, a filler, or a coalescent.

Another embodiment of the invention provides a coating composition as any embodiment above wherein the coating composition is substantially free of a biocide.

The details of one or more examples are set forth in the accompanying drawings and the description below. Other features, objects, and advantages of the disclosure will be apparent from the description and drawings, and from the claims.

DETAILED DESCRIPTION

A "latex" polymer means a dispersion or emulsion of polymer particles formed in the presence of water and one or more dispersing or emulsifying agents (e.g., a surfactant, alkali-soluble polymer, or mixtures thereof) whose presence is required to form the dispersion or emulsion. The dispersing or emulsifying agent is typically separate from the polymer after polymer formation. In some examples, a reactive dispersing or emulsifying agent may become part of the polymer particles as they are formed.

The recitation of a numerical range using endpoints includes all numbers subsumed within that range (e.g., 1 to 5 includes 1, 1.5, 2, 2.75, 3, 3.80, 4, 5, etc.).

The terms "a," "an," "the," "at least one," and "one or more" are used interchangeably. Thus, for example, a coating composition that contains "an" additive means that the coating composition includes "one or more" additives.

The phrase "low VOC" when used with respect to a liquid coating composition means that the liquid coating composition contains less than about 150 g/L (about 15% w/v), preferably not more than about 100 g/L (about 10% w/v), more preferably not more than about 50 g/L (about 5% w/v), and most preferably less than 20 g/L (about 2% w/v), for example not more than about 10 g/L (about 1% w/v) or not more than about 8 g/L (about 0.8% w/v) volatile organic compounds.

The term "(meth)acrylic acid" includes either or both of acrylic acid and methacrylic acid, and the term "(meth) acrylate" includes either or both of an acrylate and a methacrylate.

The terms "topcoat" or "final topcoat" refer to a coating composition which when dried or otherwise hardened provides a decorative or protective outermost finish layer on a substrate, for example, a polymeric membrane attached to a building exterior (e.g., a roof). By way of further explanation, such final topcoats include paints, stains or sealers capable of withstanding extended outdoor exposure (e.g., exposure equivalent to one year of vertical south-facing Florida sunlight) without visually objectionable deterioration, but do not include primers that would not withstand extended outdoor exposure if left uncoated with a topcoat.

The disclosure describes coating formulations and coatings that include bacteria that exhibit biologically induced mineralization (BIM) or biologically controlled mineralization (BCM) of calcium carbonate ($CaCO_3$) using the ChaA antiporter protein. The coating formulations and coatings may be polymer-based, such as, for example, latex coatings, solution polymer coatings, epoxy coatings, polyurethane coatings, or the like. The polymer-based coatings include large organic (i.e., carbon-containing) content, in comparison to inorganic materials such as concrete or cement. The coating formulations may be used to form coatings that exhibit self-healing properties in response to damage, such as a cut, tear, puncture, abrasion, or the like. For example, in response to being exposed to the damage, the bacteria may utilize nutrients, a calcium source, and water to cause precipitation of calcium carbonate at the site of the damage. The nutrients, the calcium source, and the water may be provided as part of the coating formulation, as part of another layer of a coating system, from an external source (e.g., an applied spray or wash), or combinations thereof. The precipitated calcium carbonate may result in a substantially opaque material that at least partially fills the damage, resulting in a repaired coating.

The BIM or BCM process using the ChaA antiporter protein also may incorporate bicarbonate ions from atmospheric carbon dioxide using the YadF carbonic anhydrase, which derives $HCO_3^-$ from atmospheric $CO_2$. In this way, the BIM or BCM process incorporates additional mass and volume from outside the coating during the repair process, reducing or substantially eliminating the need for additional carbon source in the coating formulation and coating. This may result in a coating with mechanical properties more similar to those of coatings that do not include bacteria, as compared to bacteria that exhibit BIM via the urease-based cleavage of urea, which may require substantial quantities of organic material that can significantly weaken the coating. Additionally, or alternatively, incorporation of mass from outside the coating may reduce or substantially eliminate mass-moving limitations that arise in other self-healing process, such as those that use encapsulated healing payloads (such as reactive monomers) to provide material for the healing of the coating.

The coating formulations described herein may be used to form coatings that enable permanent repair of coating damage using self-healing calcium carbonate precipitation. The repaired portion may be visibly opaque due to the presence of calcium carbonate, such that the damage is obscured. The repaired portion also may possess mechanical properties the same or nearly the same as the original coating, such that the repaired coating has relatively little or even no loss of strength compared to the original coating.

Additionally, as the coatings described herein include bacteria that incorporate bicarbonate ions from atmospheric carbon dioxide using the YadF carbonic anhydrase, which derives $HCO_3^-$ from atmospheric $CO_2$, the coatings may act as carbon sequesters. Because the carbon is incorporated into calcium carbonate, which may be stable on geological timeframes, the coatings may be effective at reducing atmospheric carbon dioxide levels, particularly as compared to other coatings that release carbon dioxide during formation or self-repairing processes.

Figure 1:
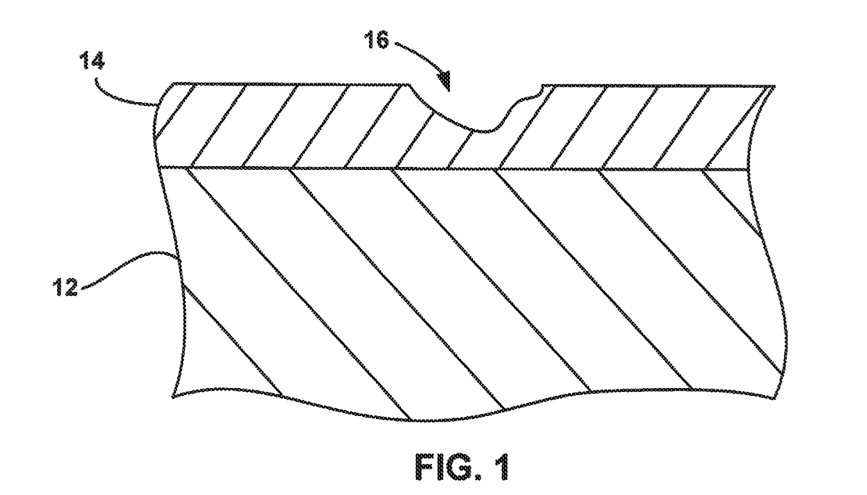
FIG. 1 is a conceptual cross-sectional view of a substrate coated with a coating layer in accordance with examples of this disclosure.

FIG. 1 illustrates a coating layer 14 on a substrate 12. Substrate 12 may include any material to be coated, including, for example, wood, a wood-derived product, an engineered wood product, concrete, plaster, drywall, paper, metal, polymer, or the like. Coating layer 14 may be deposited from a coating formulation. The coating formulation may include a polymeric binder and, optionally, a carrier liquid. The coating formulation also may include one or more optional additives, such as, for example, a pigment or colorant, a dispersant, a fungicide, an UV stabilizer, a thickener, a wetting agent, a defoamer, a filler, a coalescent, or combinations thereof. In some examples, the coating formulation is substantially free (e.g., free or nearly free) of a biocide, or the coating formulation may include a biocide that is selected to allow growth of the bacteria used in the BIM or BCM of calcium carbonate.

The polymeric binder may include any suitable polymeric binder. The polymeric binder may include, for example, a polymeric binder used in a paint formulation, a clear-coat formulation, a stain formulation, a sealant formulation, or the like, and may be used in a water-based formulation or a solvent-free formulation. The polymeric binder may be present in a carrier liquid in some examples, and may be dispersed in the carrier liquid (e.g., in an emulsion stabilized colloidally or using a surfactant), present as a solute in the carrier liquid (e.g., in a solution polymer), or the like.

In some examples, the polymer binder may be based on epoxy chemistry, polyurethane chemistry, latex chemistry, (meth)acrylate chemistry, acetate chemistry (e.g., ethylene-vinyl acetate), or the like. The polymer binder may be synthetic or may be a naturally occurring polymer, biological polymer, or a bio-based polymer, such as a polysaccharide, a polypeptide, a lipid, a nucleic acid-based polymer, either crosslinked or uncrosslinked. Some example polymer binders include poly(ethylene-vinyl acetate) "PEVA," a vinyl ester homopolymer or copolymer, a silane or fluorine containing latex emulsion, or the like. For example, the polymeric binder may include a latex-based paint formulation and may include a polymeric binder including a latex copolymer that is surfactant or colloidally stabilized in the latex emulsion.

The latex copolymer may be an emulsion polymerized latex copolymer and may be formed from reactants that include at least one emulsion polymerized ethylenically unsaturated monomer. The reactants used to form the emulsion polymerized latex copolymer may include a (meth) acrylate component, a vinyl component, a styrene component, an ester component, a urethane component, an amide component, a chlorinated olefin component, a saturated or unsaturated alkyl component, or the like, or combinations thereof.

In some examples, the reactants that form the latex copolymer also include an ethylenically unsaturated ionic monomer component or an at least partially neutralized ethylenically unsaturated ionic monomer component. The at least partially neutralized ethylenically unsaturated ionic monomer component may be a salt form of the ethylenically unsaturated ionic monomer component, and the salt form may be formed prior to, during, or after reaction of the ethylenically unsaturated ionic monomer component with the other monomer components in the reactants to form the latex copolymer.

In some examples, the ethylenically unsaturated ionic monomer component may include an acid- or anhydride-functional ethylenically unsaturated monomer or an at least partially neutralized acid- or anhydride-functional ethylenically unsaturated monomer. For example, the ethylenically unsaturated ionic monomer component may include acrylic acid, methacrylic acid, crotonic acid, fumaric acid, maleic acid, 2-methyl maleic acid, itaconic acid, 2-methyl itaconic acid, anhydride variants thereof, at least partially neutralized variants thereof, or combinations thereof.

In some examples, the reactants that form the latex copolymer also may include a chain transfer agent. The chain transfer agent may include any suitable chain transfer agent, such as a thiol. In some examples, the chain transfer agent includes or consists of a mercaptan, such as dodecyl mercaptan.

In some examples, the reactants further include a ureido-functional monomer. The ureido-functional monomer may affect adhesion of the latex copolymer to substrates. In some examples, the ureido-functional monomer includes a ureido-functional ethylenically unsaturated monomer, such as a ureido-functional methacrylic monomer.

In some examples, the reactants further include a seed latex. The seed latex may function as a polymerization growth site and may affect a final particle size of the latex copolymer The latex copolymers disclosed above may, in some examples, be formed and/or stabilized with one or more emulsifiers (e.g., surfactants), used either alone or together. Examples of suitable nonionic emulsifiers include tert-octylphenoxyethylpoly(39)-ethoxyethanol, dodecyloxypoly(10)ethoxyethanol, nonylphenoxyethyl-poly(40)ethoxyethanol, polyethylene glycol 2000 monooleate, ethoxylated castor oil, fluorinated alkyl esters and alkoxylates, polyoxyethylene (20) sorbitan monolaurate, sucrose monococoate, di(2-butyl) phenoxypoly(20)ethoxvethanol, hydroxyethylcellulosepolybutyl acrylate graft copolymer, dimethyl silicone polyalkylene oxide graft copolymer, poly(ethylene oxde)poly(butyl acrylate) block copolymer, block copolymers of propylene oxide and ethylene oxide, 2,4,7,9-tetranethyl-5-decyne-4,7-diol ethoxylated with ethylene oxide, N-polyoxyethylene(20)lauranide, N-lauryl-N-polyoxyethylene(3)anine and poly(10)ethylene glycol dodecyl thioether. Examples of suitable anionic emulsifiers include sodium lauryl sulfate, sodium dodecylbenzenesulfonate, potassium stearate, sodium dioctyl sulfosuccinate, sodium dodecyldiphenyloxide disulfonate, nonylphenoxyethylpoly(1)ethoxyethyl sulfate ammonium salt, sodium styrene sulfonate, sodium dodecyl allyl sulfosuccinate, linseed oil fatty acid, sodium potassium, or ammonium salts of phosphate esters of ethoxylated nonylphenol or tridecyl alcohol, sodium octoxynol-3-sulfonate, sodium cocoyl sarcocinate, sodium I-alkoxy-2-hydroxypropyl sulfonate, sodium alpha-olefin $(C_{14}-C_{16})$sulfonate, sulfates of hydroxyalkanols, tetrasodium N-(1,2-dicarboxy ethyl)-N-octadecylsulfosuccinamate, disodium N-octadecylsulfosuccinamate, disodium alkylamido poly-ethoxy sulfosuccinate, disodium ethoxylated nonylphenol half ester of sulfosuccinic acid and the sodium salt of tert-octylphenoxyethoxypoly(39)ethoxyethyl sulfate.

The latex copolymer may be polymerized using chain growth polymerization. One or more water-soluble free radical initiators may be used in the chain growth polymerization. Initiators suitable for use in the coating compositions will be known to persons having ordinary skill in the art or can be determined using standard methods. Representative water-soluble free radical initiators include hydrogen peroxide; tert-butyl peroxide; alkali metal persulfates such as sodium, potassium and lithium persulfate; ammonium persulfate; and mixtures of such initiators with a reducing agent. Representative reducing agents include sulfites such as alkali metal metabisulfite, hydrosulfite, and hyposulfite; sodium formaldehyde sulfoxylate; and reducing sugars such as ascorbic acid and isoascorbic acid.

In some examples, rather than being a latex copolymer, the polymeric binder may include an epoxy. An epoxy may be a two-part formulation including a resin component and a co-reactant or hardener. The resin component may include, for example, bisphenol A, bisphenol F, a phenolic novolac, or the like. The co-reactant or hardener may include, for example, an amine or amide, such as a polyamide, an amidoamine, a phenalkamine, a cycloaliphatic amine, an aromatic amine, an aliphatic amine, an aliphatic amine adduct, or the like.

In some examples, the polymeric binder may include a polyurethane. The polyurethane may be a one-part or a two-part formulation and may be dispersed in an aqueous carrier.

In some examples, the coating formulation may include at least one additive in addition to the polymeric binder. The at least one additive may include, for example, a coalescent, a dispersant, a fungicide, an UV stabilizer, a thickener, a wetting agent, a defoamer, a filler, a pigment or colorant, or combinations thereof.

The coating formulation may contain one or more optional ingredients that are VOCs. Such ingredients will be known to persons having ordinary skill in the art or can be determined using standard methods. Desirably, the coating compositions are low VOC, and preferably include less than 150 g/L (about 15% w/v), preferably not more than about 100 g/L (about 10% w/v), more preferably not more than about 50 g/L (about 5% w/v), and most preferably less than 20 g/L (about 2% w/v), for example not more than about 10 g/L (about 1% w/v) or not more than about 8 g/L (about 0.8% w/v) volatile organic compounds.

The coating formulations may contain one or more optional coalescents to facilitate film formation. Coalescents suitable for use in the coating formulations will be known to persons having ordinary skill in the art or can be determined using standard methods. Exemplary coalescents include glycol ethers such those sold under the trade names as EASTMAN™ EP, EASTMAN™ DM, EASTMAN™ DE, EASTMAN™ DP, EASTMAN™ DB and EASTMAN™ PM from Eastman Chemical Company, Kingsport, Tenn., and ester alcohols such as those sold under the trade names TEXANOL™ ester alcohol from Eastman Chemical Company. The optional coalescent may be a low VOC coalescent such as is described in U.S. Pat. No. 6,762,230 B2. The coating formulations may include a low VOC coalescent in an amount of at least about 0.5 parts by weight, or at least about 1 part by weight, and or at least about 2 parts by weight, based on a total non-volatile weight of the coating formulations. The coating formulations also may include a low VOC coalescent in an amount of less than about 10 parts by weight, or less than about 6 parts by weight, or less than about 4 parts by weight, based on a total non-volatile weight of the coating formulations.

Other optional additives for use in the coating formulations described herein are described in Koleske et al., Paint and Coatings Industry, April, 2003, pages 12-86. Some performance enhancing additives that may be employed include coalescing solvent(s), defoamers, dispersants, amines, preservatives, biocides, mildewcides, fungicides, glycols, surface active agents, pigments, colorants, dyes, surfactants, thickeners, heat stabilizers, leveling agents, anti-cratering agents, curing indicators, plasticizers, fillers, sedimentation inhibitors, ultraviolet-light absorbers, optical brighteners, and the like to modify properties of the coating formulations.

The disclosed coating formulations may include a surface-active agent (surfactant) that modifies the interaction of the coating formulations with the substrate or with a prior applied coating. The surface-active agent affects qualities of the coating formulations including how the coating formulations is handled, how it spreads across the surface of the substrate, and how it bonds to the substrate. The surface-active agent can modify the ability of the coating formulations to wet a substrate and also may be referred to as a wetting agent. Surface-active agents may also provide leveling, defoaming, or flow control properties, and the like. If the coating formulations include a surface-active agent, the surface-active agent is preferably present in an amount of less than 5 weight %, based on the total weight of the coating formulations. Surface-active agents suitable for use in the coating formulations will be known to persons having ordinary skill in the art or can be determined using standard methods. Some suitable surface-active agents include those available under the trade designations STRODEX™ KK-95H, STRODEX™ PLF100, STRODEX™ PK0VOC, STRODEX™ LFK70, STRODEX™ SEK50D and DEXTROL™ OC50 from Dexter Chemical L.L.C., Bronx, N.Y.; HYDROPALAT™ 100, HYDROPALAT™ 140, HYDROPALAT™ 44, HYDROPALAT™ 5040 and HYDROPALAT™ 3204 from Cognis Corporation, Cincinnati, Ohio; LIPOLIN™ A, DISPERS™ 660C, DISPERS™ 715W and DISPERS™ 750W from Degussa Corporation, Parsippany, N.J.; BYK™ 156, BYK™ 2001 and ANTI-TERRA™ 207 from Byk Chemie, Wallingford, Conn.; DISPEX™ A40, DISPEX™ N40, DISPEX™ R50, DISPEX™ G40, DISPEX™ GA40, EFKA™ 1500, EFKA™ 1501, EFKA™ 1502, EFKA™ 1503, EFKA™ 3034, EFKA™ 3522, EFKA™ 3580, EFKA™ 3772, EFKA™ 4500, EFKA™ 4510, EFKA™ 4520, EFKA™ 4530, EFKA™ 4540, EFKA™ 4550, EFKA™ 4560, EFKA™ 4570, EFKA™ 6220, EFKA™ 6225, EFKA™ 6230 and EFKA™ 6525 from Ciba Specialty Chemicals, Tarrytown, N.Y.; SURFYNOL™ CT-111, SURFYNOL™ CT-121, SURFYNOL™ CT-131, SURFYNOL™ CT-211, SURFYNOL™ CT 231, SURFYNOL™ CT-136, SURFYNOL™ CT-151, SURFYNOL™ CT-171, SURFYNOL™ CT-234, CARBOWET™ DC-01, SURFYNOL™ 104, SURFYNOL™ PSA-336, SURFYNOL™ 420, SURFYNOL™ 440, ENVIROGEM™ AD-01 and ENVIROGEM AE01 from Air Products & Chemicals, Inc., Allentown, Pa.; TAMOL™ 1124, TAMOL 850, TAMOL 681, TAMOL™ 731 and TAMOL™ SG-1 from Rohm and Haas Co., Philadelphia, Pa.; IGEPAL™ CO-210, IGEPAL™ CO-430, IGEPAL™ CO-630, IGEPAL™ CO-730, and IGEPAL™ CO-890 from Rhodia Inc., Cranbury, N.J.; T-DET™ and T-MULZ™ products from Harcros Chemicals Inc., Kansas City, Kans.; polydimethylsiloxane surface-active agents (such as those available under the trade designations SILWET™ L-760 and SILWET™ L-7622 from OSI Specialties, South Charleston, W. Va., or BYK™ 306 from Byk-Chemie) and fluorinated surface-active agents (such as that commercially available as FLUORAD™ FC-430 from 3M Co., St. Paul, Minn.).

In some examples, the surface-active agent may be a defoamer. Some suitable defoamers include those sold under the trade names BYK™ 018, BYK™ 019, BYK™ 020, BYK™ 022, BYK™ 025, BYK™ 032, BYK™ 033, BYK™ 034, BYK™ 038, BYK™ 040, BYK™ 051, BYK™ 060, BYK™ 070, BYK™ 077 and BYK™ 500 from Byk Chemie; SURFYNOL™ DF-695, SURFYNOL™ DF-75, SURFYNOL™ DF-62, SURFYNOL™ DF-40 and SURFYNOL™ DF-110D from Air Products & Chemicals, Inc.; DEEFO™ 3010A, DEEFO™ 2020E/50, DEEFO™ 215, DEEFO™ 806-102 and AGITAN™ 31BP from Munzing Chemie GmbH, Heilbronn, Germany; EFKA 2526, EFKA 2527 and EFKA 2550 from Ciba Specialty Chemicals; FOAMAX™ 8050, FOAMAX™ 1488, FOAMAX™ 7447, FOAMAX™ 800, FOAMAX™ 1495 and FOAMAX 810 from Degussa Corp.; FOAMASTER™ 714, FOAMASTER™ A410, FOAMASTER™ 111, FOAMASTER™ 333, FOAMASTER™ 306, FOAMASTER™ SA-3, FOAMASTER™ AP, DEHYDRAN™ 1620, DEHYDRAN™ 1923 and DEHYDRAN™ 671 from Cognis Corp.

The coating formulations also may contain one or more optional pigments or colorants. Pigments suitable for use in the coating compositions will be known to persons having ordinary skill in the art or can be determined using standard methods. Some suitable pigments include titanium dioxide white, calcium carbonate, carbon black, lampblack, black iron oxide, red iron oxide, yellow iron oxide, brown iron oxide (a blend of red and yellow oxide with black), phthalocyanine green, phthalocyanine blue, organic reds (such as naphthol red, quinacridone red and toulidine red), quinacridone magenta, quinacridone violet, DNA orange, or organic yellows (such as Hansa yellow). In some examples, the coating formulation is a white or light-colored coating formulation and includes titanium dioxide, calcium carbonate, yellow iron oxide, organic yellow, or the like. The coating formulation can also include a gloss control additive or an optical brightener, such as that commercially available under the trade designation UVITEX™ OB from Ciba-Geigy.

In some examples, the coating formulations may include an optional filler or inert ingredient. Fillers or inert ingredients extend, lower the cost of, alter the appearance of, or provide desirable characteristics to the coating formulations before and after drying. Fillers and inert ingredients suitable for use in the coating formulations will be known to persons having ordinary skill in the art or can be determined using standard methods. Some suitable fillers or inert ingredients include, for example, clay, glass beads, calcium carbonate, talc, silicas, feldspar, mica, barytes, ceramic microspheres, calcium metasilicates, organic fillers, and the like.

In certain applications it may also be desirable to include in the coating formulations a fungicide or the like. The coating formulations may be substantially free (e.g., free or nearly free) of biocides, or may include a biocide selected to allow growth of the bacteria that exhibit BIM or BCM of calcium carbonate. Example biocides include antibacterial agents. Biocides have bacteriostatic and bactericidal properties.

The coating formulations may also include other ingredients that modify properties of the coating formulations as it is stored, handled, or applied, and at other or subsequent stages. Waxes, flatting agents, rheology control agents, mar and abrasion additives, and other similar performance enhancing additives may be employed as needed in amounts effective to upgrade the performance of the dried coating and the coating formulations. Some suitable wax emulsions to improve coating physical performance include those sold under the trade names MICHEM™ Emulsions 32535, 21030, 61335, 80939M and 7173MOD from Michelman, Inc. Cincinnati, Ohio and CHEMCOR™ 20N35, 43A40, 950C25 and 10N30 from ChemCor of Chester, N.Y. Some suitable rheology control agents include those sold under the trade names RHEOVIS™ 112, RHEOVIS™ 132, RHEOVIS™, VISCALEX™ HV30, VISCALEX™ AT88, EFKA 6220 and EFKA 6225 from Ciba Specialty Chemicals; BYK™ 420 and BYK™ 425 from Byk Chemie; RHEOLATE™ 205, RHEOLATE™ 420 and RHEOLATE™ 1 from Elementis Specialties, Hightstown, N.J.; ACRYSOL™ L TT-615, ACRYSOL™ RM-5, ACRYSOL™ RM-6, ACRYSOL™ RM-8W, ACRYSOL™ RM-2020 and ACRYSOL™ RM-825 from Rohm and Haas Co.; NATROSOL™ 250LR from Hercules Inc., Wilmington, Del. and CELLOSIZE™ QP09L from Dow Chemical Co., Midland, Mich. Desirable performance characteristics of the coating include adhesion, chemical resistance, abrasion resistance, hardness, gloss, reflectivity, appearance, or combinations of these characteristics, and other similar characteristics. For example, the coating formulations may include abrasion resistance promoting adjuvants such as silica or aluminum oxide (e.g., sol gel processed aluminum oxide).

In certain applications it may also be desirable to include in the coating formulations an optional UV stabilizer. Concentration of the optional UV stabilizer in the coating formulations will be known to persons having ordinary skill in the art or can be determined using standard methods. UV stabilizers may include encapsulated hydroxyphenyl-triazine compositions and other compounds known to persons having ordinary skill in the art, for example, TINUVIN™ 477DW, commercially available from BASF Corporation.

In some examples, the coating formulations may optionally a thickener. Thickeners may include hydroxyethyl cellulose; hydrophobically modified ethylene oxide urethane; processed attapulgite, a hydrated magnesium aluminosilicate; and other thickeners known to persons having ordinary skill in the art. For example, thickeners may include CELLOSIZE™ QP-09-L and ACRYSOL™ RM-2020NPR, available from Dow Chemical Company; and ATTAGEL™ 50, available from BASF Corporation. Concentration of the optional thickener stabilizer in the coating formulations will be known to persons having ordinary skill in the art or can be determined using standard methods.

The coating formulations also may include bacteria that exhibit BIM or BCM of calcium carbonate ($CaCO_3$). The bacteria may include Gram-positive or Gram-negative bacteria. The bacteria may be vegetative or spores. The bacteria may include naturally occurring bacteria, modified bacteria, genetically modified bacteria, or combinations thereof. In some examples, the bacteria include members of the phyla Proteobacteria or Firmicutes, or an Actinomycetales (an order of Actinobacteria).

The bacteria used in the coating formulations of this disclosure exhibit BIM or BCM of calcium carbonate ($CaCO_3$) that may be mediated by the ChaA antiporter protein. Intracellular $Ca^{2+}$ ions are toxic to bacteria and thus bacteria excrete $Ca^{2+}$ ions ingested from calcium-rich environments. The ChaA antiporter protein mediates the excretion of the intracellular $Ca^{2+}$ ions.

When the ability to pump out $Ca^{2+}$ ions becomes thermodynamically unfavorable (due to an increasing extracellular $Ca^{2+}$ gradient), the cell excretes excess $HCO_3^-$ (derived from atmospheric $CO_2$ via the carbonic anhydrase, YadF). A drop in pH caused by consumption of $CO_2$ and the removal of protons by ChaA leads to the spontaneous precipitation of excess $Ca^{2+}$ ions as calcite, removing excess $Ca^{2+}$ and allowing bacterial growth to continue. As such, bacteria that exhibit BIM or BCM of calcium carbonate using the ChaA antiporter protein may not require the addition of substantive quantities of organic material, urea, or both, that would potentially weaken coating layer 14, introduce unwanted effects such as malodor, or the like. Instead, the bacteria use the carbonic anhydrase YadF to generate $HCO_3^-$ from atmospheric carbon dioxide, which creates additional mass and volume in coating layer 14 during the repair process.

The bacteria may be selected to exhibit one or more selected properties. For example, the bacteria may be selected to exhibit hyper-secretion (e.g., significantly greater than average secretion) of $CaCO_3$ in the presence of calcium. The bacteria additionally or alternatively may be selected to exhibit compatibility and viability after being mixed in the coating formulation and after deposition in the coating. For example, the bacteria may exhibit viability after being mixed in the coating formulation for at least 1 hour, or at least 1 week, or at least 4 months, or at least 12 months.

Similarly, the bacteria may exhibit viability after being in the applied coating for at least 1 week, or at least 4 months, or at least 12 months.

Figure 2:
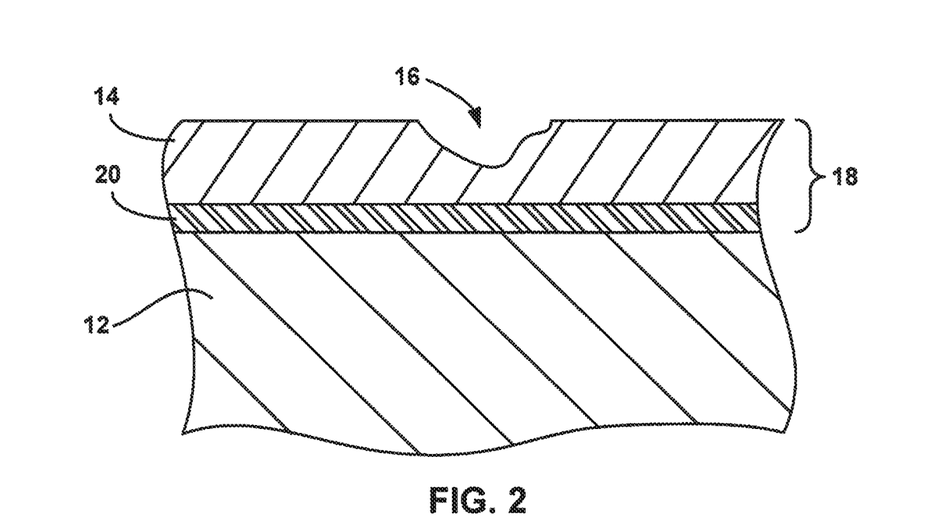
FIG. 2 is a conceptual cross-sectional view of a substrate coated with a coating system in accordance with examples of this disclosure.

In some examples, the bacteria may be mixed into the coating formulation as spores. The spores may remain inert or dormant until exposed to nutrients, water, or both, e.g., upon damage to coating layer 14. The nutrients, water, or both may cause the spores to enter the vegetative state.

In examples in which the bacteria are modified or genetically modified, the modified bacteria may exhibit enhanced calcium transport and secretion. Increased rates of calcium transport and secretion may increase the rate of filling of a damaged portion 16 of coating layer 14 with calcium carbonate; reduce microbial growth required for repairing damaged portion 16 of coating layer 14; reduce nutrients, water, or both required for repairing damaged portion 16 of coating layer 14; or combinations thereof. In some examples, if the rate of calcium transport and secretion is sufficiently enhanced (e.g., by a factor of about 1000), calcium transport and secretion may also act as a control mechanism, as the rate calcium carbonate mineralization may be sufficiently high to result in the bacteria being encapsulated by calcium carbonate, thus stopping further calcium carbonate secretion by the bacteria.

The bacteria may be incorporated in the coating formulation and, ultimately, in coating layer 14, in one or more of a variety of ways. For example, the bacteria may be mixed in the coating formulation during the manufacturing of the coating formulation. The bacteria may be directly mixed in the coating formulation as vegetative bacteria, spores, or freeze-dried bacteria. As another example, the bacteria may be encapsulated with an organic polymer encapsulant, such as alginate or polydopamine, and the encapsulated bacteria may be mixed in the coating formulation during manufacturing. As another example, the bacteria (vegetative, spores, or freeze-dried) may be mixed in the coating formulation just prior to application of the coating formulation to substrate 12. The selection of how the bacteria is incorporated in the coating formulation may be based at least in part on rheology of the coating formulation, pH of the coating formulation, visual appearance of the coating formulation, bacteria viability in the coating formulation, odor of the coating formulation, or the like.

In some examples, the bacteria may be added to the coating formulation in a concentration between about $10^2$ colony forming units per milliliter of coating formulation and about $10^6$ colony forming units per milliliter of coating formulation.

In some examples, instead of or in addition to the bacteria being incorporated in the coating formulation and coating layer 14, the bacteria may be introduced as part of the repair process for damaged portion 16, e.g., as part of a spray or wash introduced on damaged portion 16, may be incorporated into another layer of a coating system, e.g., a primer coat or an underlay, or both.

BIM or BCM of calcium carbonate using the ChaA antiporter protein and the YadF carbonic anhydrase by the bacteria may require environmental calcium, nutrients for bacterial growth, and water. The calcium source, nutrients, and water may be introduced to the bacteria using one or more of a variety of techniques.

In some examples, the calcium source may be part of coating layer 14, e.g., may be mixed in the coating formulation used to form coating layer 14. The calcium source may include calcium-containing particles, such as micro-scale calcium-containing particles (e.g., between about 1 μm and about 1 mm), nano-scale calcium-containing particles (e.g., between about 1 nm and about 1 μm, such as about 70 nm), or the like. The calcium-containing particles may include, for example, calcium carbonate, calcium titanate, a calcium aluminate, calcium silicate, or other calcium-containing minerals. In some examples, the calcium-containing particles also contribute to properties of coating layer 14 as pigments, fillers, or the like.

In some examples, the calcium source may include an organic calcium salt, an inorganic calcium salt, or combinations thereof, alone or in combination with calcium-containing particles. Example organic calcium salts include calcium propionate, and example inorganic calcium salts include calcium chloride.

The calcium source may be present in coating layer 14 (and the coating formulation from which coating layer 14 is formed) in amounts sufficient to enable the bacteria to exhibit BIM or BCM at the site of damaged portion 16. In some examples, the calcium source may be present in coating layer 14 in excess to ensure sufficient calcium is present for BIM or BCM and allow nutrients or water to be the BIM or BCM-limiting component. For example, precipitation of calcium carbonate may consume a 1:1:1 molar ratio of $Ca^{2+}$:$CO_2$:$H_2O$, so the amount of calcium present in coating layer 14 (and, more particularly, at a surface of damaged portion 16 throughout the repair process) may be selected to be in excess such that local depletion of calcium from the surface of damaged portion 16 does not lead to mass movement within coating layer 14 and thinning of other portions of coating layer 14. In some examples, the coating formulation includes between about 0.2 wt. % and about 5 wt. % of the calcium source.

In addition to, or instead of, the calcium source being present in coating layer 14, the calcium source may be present in another coating layer or may be introduced externally to coating layer 14 after the event that forms damaged portion 16. For example, as shown in FIG. 2, coating layer 14 may be part of a coating system 18 on substrate 12. Coating system may include an underlayer or primer coat 20 between coating layer 14 and substrate 12. Although only a single underlayer or primer coat 20 is illustrated in FIG. 2, in some examples, coating system 18 may include multiple underlayers or primer coats, may include one or more optional overlayers or top coats, or combinations thereof.

In some examples, the calcium source may be present in underlayer or primer coat 20 and may diffuse or otherwise be transported to damaged portion 16 in response to formation of damaged portion 16 (e.g., damaged portion 16 may extend through the thickness of coating layer 14 to expose underlayer or primer coat 18).

The calcium source also may be introduced to the surface of damaged portion 16 in a solution that is applied to coating layer 14 after formation of damaged portion 16. For example, the solution may include the calcium source and water and may be applied using spraying, wiping, or the like.

The nutrients also may be part of coating layer 14, underlayer or primer coat 18, or may be delivered separately. For example, the nutrients may be mixed in the coating formulation used to form coating layer 14, may be mixed in the coating formulation used to form underlayer or primary coat 18, or may be introduced to the surface of damaged portion 16 in a solution that is applied to coating layer 14 after formation of damaged portion 16 using spraying, wiping, or the like. In some examples in which the nutrients are included in coating layer 14 or underlayer or primer coat 18, external delivery of water to damaged portion 16 (e.g., via spraying, washing, or ambient humidity) may activate growth of the bacteria.

The nutrients may include any suitable nutrient that enables growth of the bacteria. For example, the nutrients may include non-specific mixtures of nutrients or individual, inducible co-factors, such as disaccharides (e.g., lactose), amino acids (e.g., tryptophan), carboxylic acids (e.g., acetic acid), the use of metabolites that allow for inducible regulation, such as lactose, glucose, or propionate, or the like.

In some examples, the amount of nutrients in coating layer 14, underlayer or primer coat 18, or delivered to the surface of damaged portion 16 may be selected to control growth of the bacteria and, ultimately, the precipitation of calcium carbonate. For example, the amount of nutrients may be selected to allow sufficient growth of the bacteria to allow complete optical filling of damaged portion 16, while substantially limiting growth of the bacteria to damaged portion 16, substantially limiting growth of the bacteria so that BIM or BCM ceases before the bacteria induces calcium carbonate precipitation of greater than 50 volume percent more than the volume of damaged portion 16, or combinations thereof.

Underlayer or primer coat 18 may include any suitable chemistry that promotes adhesion of coating layer 14 to substrate 12. In some examples, underlayer or primer coat 18 is a water-based coating, such as a water-based latex, acrylic, or polyurethane. In some examples, underlayer or primer coat 18 may function as a reservoir for one or more of nutrients, water, or the calcium source. Additionally, or alternatively, underlayer or primer coat 18 may include porosity that allows movement of nutrients, water, the calcium source, bacteria, or combinations thereof to the site of damaged portion 16. Porosity or hydrophilicity also may enable moisture retention in underlayer or primer coat 18. Underlayer or primer coat 18 is optional and may or may not be used with coating layer 14.

Growth of the bacteria and BIM or BCM may be controlled using one or more process controls. These process controls may include provision of water to the bacteria. For example, water may be provided to the bacteria external to coating layer 14, e.g., by wiping, spraying, rain, ambient humidity or the like. In combination with the bacteria being contained within coating layer 14, formation of damaged portion 16 may result in the bacteria being exposed to water, which may initiate growth and precipitation of calcium (e.g., in examples in which coating layer 14 includes nutrients and a calcium source).

The process controls additionally or alternatively may include nutrient delivery. For example, nutrients may be delivered external to coating layer 14, e.g., by wiping or spraying, after the event that forms damaged portion 16. As another example, nutrients may be incorporated in underlayer or primer coat 18 and may be released to damaged portion 16 in the event that damaged portion 16 extends the total thickness of coating layer 14. As another example, nutrients may be incorporated in coating layer 14 and may be encapsulated in an encapsulant, such as liposomes. The event that forms damaged portion 16 may break the encapsulant, releasing the nutrients to be accessible to the bacteria.

The process controls may utilize underlayer or primer coat 18, one or more additional underlayers or primer coats, one or more optional overcoats or top coats, or combinations thereof. For example, one or more of the calcium source, the nutrients, or water may be contained in a layer (an underlayer or an overlayer) that is separated from coating layer 14 by a spacer layer. The spacer layer may act to reduce or limit movement of the one or more of the calcium source, the nutrients, or the water into coating layer 14 in the absence of an external trigger. In this way, the spacer layer may act as a rate controlling layer that controls access by the bacteria to one or more of the calcium source, the nutrients, or water. In some examples, the external trigger may include moisture, radiation (e.g., UV, infrared, visible light, or the like), pH, or the like.

The spacer layer may include chemistry, physical configuration, or the like that affects the movement of the one or more of the calcium source, the nutrients, or water from the non-adjacent layer to coating layer 14. For example, the spacer layer may have a selected hydrophilicity or hydrophobicity, porosity, viscosity, or the like, each of which may affect rates of permeation or diffusion of the one or more of the calcium source, the nutrients, or water through the spacer layer.

In some examples, the calcium source, the nutrients, or water may be contained in different layers, and the different layers may be spaced from coating layer 14 by respective spacer layers. For example, the nutrients may be contained in an underlayer spaced from coating layer 14 by a first spacer layer, the calcium source may be contained in coating layer 14, and the water may be contained in an overlayer spaced from coating layer 14 a second spacer layer. Other configurations of underlayers, overlayers, spacer layers, coating layer 14 and distributions of water, the calcium source, and the nutrients will be apparent to a person having ordinary skill in the art.

Controls for deactivating the calcium precipitation/mineralization may include, for example, nutrient limitation, as described above, entombment of the bacteria by calcium carbonate, water limitation, or exposure of the bacteria to heat or radiation.

Figure 3:
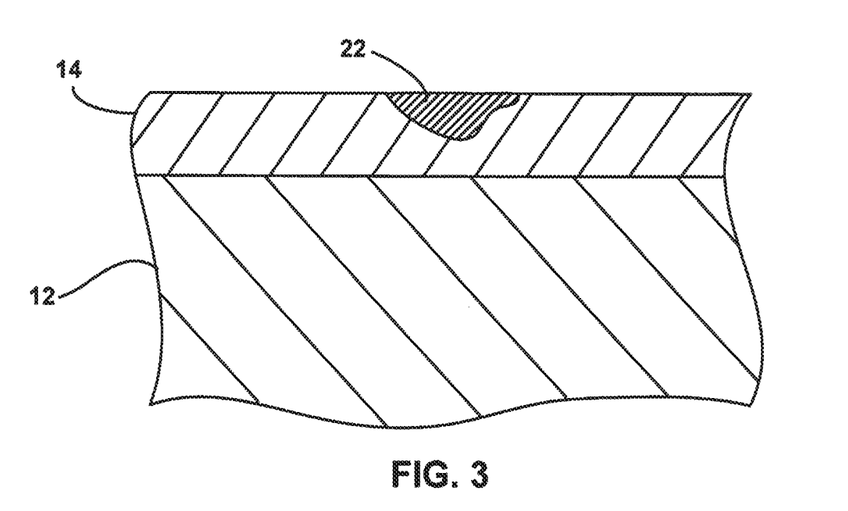
FIG. 3 is a conceptual cross-sectional view of a substrate coated with a repaired coating in accordance with examples of this disclosure.

In this way, the bacteria in coating layer 14 may exhibit BIM or BCM upon exposure to water, nutrients, and a calcium source. When controlled to occur at damaged portion 16, the BIM or BCM may fill at least part of damaged portion 16 with calcium carbonate, resulting in a repaired portion 22, shown in FIG. 3. Repaired portion 22 may be substantially optically opaque, and may have a visual appearance that depends on the polymorph of calcium carbonate that has precipitated, which may be affected by the strain of bacteria in coating layer 14, the nutrients, other environmental factors, or combinations thereof. In this way, the coating formulations and coating layer 14 described herein may enable a self-healing coating that includes a polymeric binder.

The disclosure will now be illustrated with reference to the following non-limiting examples.

EXAMPLES

Example 1: Formulation of Paint Films

Sterile water and a waterborne styrene acrylic latex emulsion were stirred at 125 rpm for about 5 min, whereupon the $CaCO_3$ powder was slowly added with continual stirring for 5 minutes. The stirring speed was increased to 525 rpm, while the thickener was added, followed by additional stirring for 8 min to make the final paint formulation. The composition is shown in Table 1.

| Component | Vehicle | Initial Solids (%) | Mass (g) | Volume (ml) | Final Solids (%) |
|---|---|---|---|---|---|
| H$_2$O | N/A | 0 | N/A | 9.9 | 0.0 |
| Waterborne Styrene Acrylic Latex | Water | 42 | N/A | 10 | 21.0 |
| ALBAFIL T-10 Precipitated CaCO$_3$ | Water | 100 | 1 | N/A | 5.0 |
| 33% TT Thickener | Water | 9.9 | N/A | 0.1 | 0.0 |
| Total | | | | 20 | 26.0 |

Figure 4:
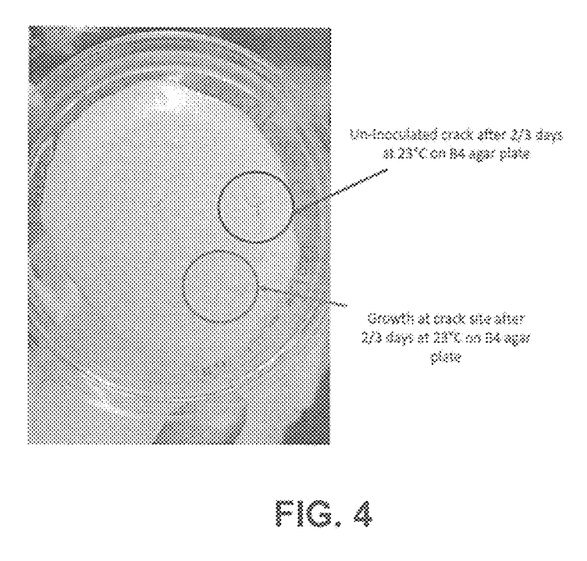
FIG. 4 is an image of an example styrene acrylic latex coating on a Boquet B4 media plate.

The paint film was made by pouring the paint onto a sterile polypropylene surface. The paint films were allowed to dry in a Labconco Purifier Class II Biosafet cabinet (available from Thermo Fisher Scientific, Waltham, Mass.) for 12 hours. The paint film was peeled off the surface and placed onto a Boquet B4 media plate (containing about 1.0 wt. % glucose, about 0.4 wt %. yeast extract, about 0.25 wt. % calcium acetate, and about 1.5 wt. % agar). FIG. 4 is an image of the paint film, which includes cracks in the paint film created through drying.

Example 2: Use of a Microbial Sealing Wash

Figure 5A:
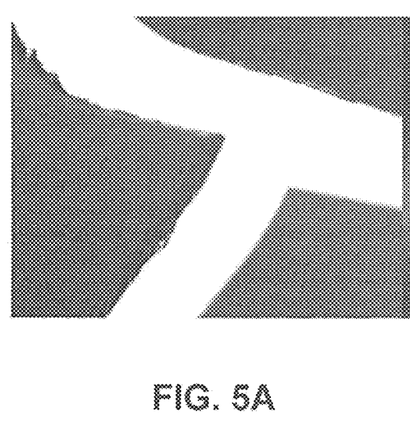
FIG. 5A is a micrograph of an example styrene acrylic latex styrene acrylic coating spotted with bacteria after zero hours of bacteria growth.
Figure 5B:
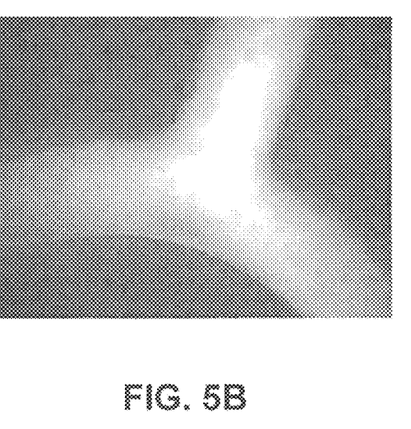
FIG. 5B is a micrograph of an example styrene acrylic latex coating spotted with bacteria after 72 hours of bacteria growth.

10 μL of a 1×10$^8$ cells/mL culture of *Bacillus* str. P6A (Banks et al., 2010) in tryptic soy broth (TSB) was used to spot a corner of the crack. The ability of the bacteria to grow across the surface of the paint film was monitored at 21° C. The images in FIGS. 5A and 5B were taken on a Stereomaster dissecting microscope (available from Thermo Fisher Scientific) at 30× with back-lighting. FIG. 5A is a micrograph of the paint film showing the crack at 0 hours, and FIG. 5B is a micrograph of the same paint film and crack after 72 hours. The observed opacity is FIG. 5B is from the deposition of calcium carbonate by bacteria within the crack.

Example 3: Bacteria Embedded in Paint Films

A paint formulation was prepared according to the procedure described with reference to Example 1. After formulation of the final paint composition, an overnight culture of *Bacillus* str. P6A was introduced to the prepared paint composition to a final concentration of 1×10$^6$ cells/mL of paint formulation. The paint composition including the bacteria was gently stirred at 125 rpm for about 1 min.

Figure 6A:
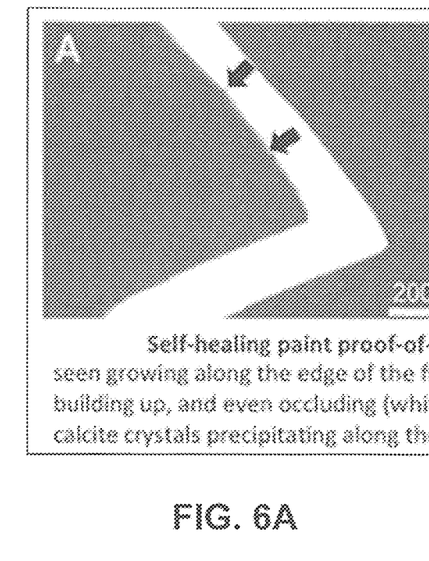
FIGS. 6A-6C are micrographs of an example styrene acrylic latex coating with incorporated bacteria after 0 hours, 48 hours, and 1 week, respectively.
Figure 6B:
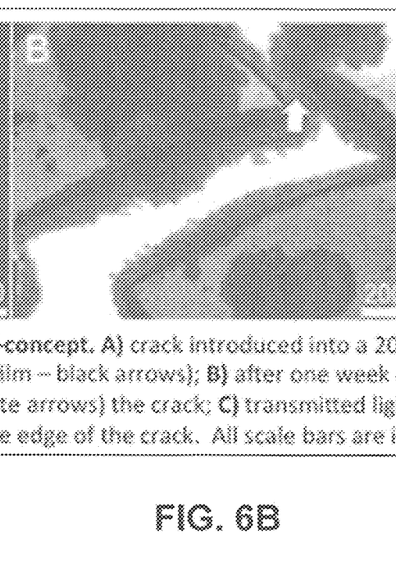
Figure 6C:
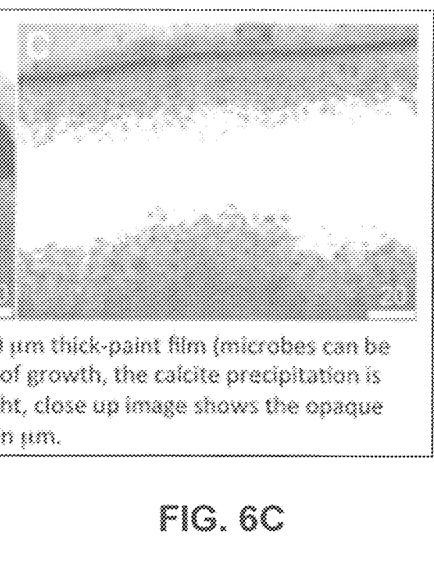

The paint film was made by pouring the paint onto a sterile polypropylene surface. The paint films were allowed to dry in a Labconco Purifier Class II Biosafet cabinet (available from Thermo Fisher Scientific, Waltham, Mass.) for 12 hours. Once the paint film had dried it was applied to the Boquet B4 media and monitored for growth at 21° C. Growth of the bacteria on the plate was monitored by light microscopy on an Olympus BX53 microscope (available from Olympus America Inc., Center Valley, Pa.) at 100× (FIGS. 6A and 6B) and 400× (FIG. 6C). Precipitation of calcium carbonate was observed after 0 hours (FIG. 6A), 48 hours (FIG. 6B) and 1 week (FIG. 6C). The top-lit images (FIGS. 6A and 6B) indicate the growth of bacteria (indicated by the opaque/dark material), while the opaque material in the back-lit image (FIG. 6C) demonstrates the calcium carbonate precipitates. The ability of bacterially precipitated calcium carbonate to occlude the crack in the paint can be observed in FIG. 6B, with the encroaching precipitated calcium carbonate shown in FIG. 6C.

Various examples have been described. These and other examples are within the scope of the following claims.

What is claimed is:

1. A coating composition comprising:
    a polymeric binder comprising at least one of a (meth) acrylic latex, a vinyl acrylic latex, a styrene acrylic latex, or a polyurethane; and
    bacteria that exhibit biologically induced mineralization or biologically controlled mineralization of calcium carbonate in the presence of environmental calcium.

2. The coating composition of claim 1, wherein the bacteria comprise vegetative bacteria.

3. The coating composition of claim 1, wherein the bacteria comprise spores.

4. The coating composition of claim 1, wherein the bacteria comprise genetically modified bacteria configured to exhibit enhanced calcium transport and secretion.

5. The coating composition of claim 1, wherein the bacteria are encapsulated in an encapsulant.

6. The coating composition of claim 5, wherein the encapsulant comprises alginate or polydopamine.

7. The coating composition of claim 1, comprising between about 10$^2$ colony forming units per milliliter and about 10$^6$ colony forming units per milliliter.

8. The coating composition of claim 1, further comprising a calcium source.

9. The coating composition of claim 8, wherein the calcium source comprises calcium carbonate particles.

10. The coating composition of claim 8, comprising between about 0.2 wt. % and about 5 wt. % of the calcium source.

11. A coating composition of claim 1, further comprising:
    a polymeric binder;
    nutrients; and
    bacteria that exhibit biologically induced mineralization or biologically controlled mineralization of calcium carbonate in the presence of environmental calcium.

12. The coating composition of claim 11, wherein the nutrients comprise at least one of a disaccharide, an amino acid, or a carboxylic acid.

13. The coating composition of claim 1, wherein the polymeric binder comprises at least one of a (meth)acrylic latex, a vinyl acrylic latex, or a styrene acrylic latex.

14. The coating composition of claim 1, wherein the polymeric binder comprises a polyurethane.

15. A coating composition comprising:
    a polymeric binder;
    an aqueous carrier liquid; and
    bacteria that exhibit biologically induced mineralization or biologically controlled mineralization of calcium carbonate in the presence of environmental calcium.

16. The coating composition of claim 1, further comprising an additive selected from a pigment, a colorant, a dispersant, a fungicide, an UV stabilizer, a thickener, a wetting agent, a defoamer, a filler, or a coalescent.

17. The coating composition of claim 1, wherein the coating composition is free of a biocide.

18. An article comprising:
    a substrate; and
    a coating system on the substrate, wherein the coating system comprises:
        a coating layer comprising:
            a polymeric binder comprising at least one of a (meth)acrylic latex, a vinyl acrylic latex, a styrene acrylic latex, or a polyurethane and bacteria that exhibit biologically induced mineralization or biologically controlled mineralization of calcium carbonate in the presence of environmental calcium nutrients, and an additive comprising at least one of a pigment, a colorant, a dispersant, a fungicide, an UV stabilizer, a thickener, a wetting agent, a defoamer, a filler, or a coalescent; and a calcium source.

19. The article of claim 18, further comprising an underlayer or primer coat, wherein the underlayer or primer coat is between the substrate and the coating layer, and wherein the underlayer or primer coat comprises the calcium source.

\* \* \* \* \*